United States Patent [19]
McEwan

[11] Patent Number: 5,986,600
[45] Date of Patent: Nov. 16, 1999

[54] PULSED RF OSCILLATOR AND RADAR MOTION SENSOR

[76] Inventor: Thomas E. McEwan, 1734 Cairo St., Livermore, Calif. 94550

[21] Appl. No.: 09/073,159

[22] Filed: May 5, 1998

Related U.S. Application Data

[60] Provisional application No. 60/072,136, Jan. 22, 1998.

[51] Int. Cl.⁶ ..................................................... G01S 13/56
[52] U.S. Cl. ............................................. 342/28; 342/175
[58] Field of Search ................................. 342/28, 27, 22, 342/68, 175, 194, 203, 204; 331/117 FE, 173

[56] References Cited

U.S. PATENT DOCUMENTS

| | | | |
|---|---|---|---|
| 4,197,537 | 4/1980 | Follen et al. | |
| 4,755,772 | 7/1988 | Khanna | 331/109 |
| 5,682,164 | 10/1997 | McEwan | 342/28 |

*Primary Examiner*—Daniel T. Pihulic
*Attorney, Agent, or Firm*—Haynes & Beffel LLP

[57] ABSTRACT

A pulsed RF oscillator employing a BIAS-ON path and a QUENCH path to produce fast turn-on and fast turn-off RF bursts with well-controlled burst width. The oscillator further includes amplitude and stability control elements, and a 5.8 GHz microstrip implementation is disclosed. The pulsed RF oscillator can be configured with quadrature RF homodyne detectors to form a range-gated pulse-Doppler motion sensor system for sensing target motion within a gated region. The sensor includes a transmitter for transmitting a sequence of RF bursts comprised of a number of cycles at the transmitter frequency. The sensor further includes a receiver responsive to the transmitted bursts and burst echoes from moving targets within its sensing field. The receiver produces Doppler signal with an amplitude representative sum of the transmitted burst and the echo burst. A Doppler motion response occurs for moving targets within a region sharply defined by the transmitted burst width. Another mode provides a quadrature receiver channel for target direction determination. Yet another mode time-sequences the transmitted burst widths to provide multiple range cell operation.

57 Claims, 6 Drawing Sheets

PULSED RF OSCILLATOR AND RADAR MOTION SENSOR

RELATED APPLICATIONS

This application incorporates by reference as if fully set forth herein, and claims the benefit under 35 U.S.C. §119(e) of United States Provisional patent application No. 60/072, 136, filed on Jan. 20, 1998, entitled "Multi-Channel Field Disturbance Sensor", having inventor Thomas E. McEwan.

BACKGROUND OF THE INVENTION

1. Field of the Invention

The present invention relates to pulsed oscillators such as those used in electronic sensors, like radar sensors utilizing pulse-echo range gating for target motion detection.

2. Description of Related Art

Continuous Wave CW Doppler radar motion sensors emit a continuous wave carrier and mix the transmitted radio frequency RF with the return echoes to produce a difference frequency equal to the Doppler shift produced by a moving target. CW Doppler sensors have a number of serious deficiencies that limit their widespread application: 1) lack of a definite range limit, which leads to false triggers on distant clutter, 2) high current consumption due to CW operation, making battery operation impractical, and 3) inability to collocate sensors due to mutual interference.

Amplitude Modulated AM, or pulse, Doppler motion sensors have been described in U.S. Pat. No. 4,197,537 by Follen et al., in U.S. Pat. No. 5,682,164 by McEwan, and others. In pulse Doppler, a short pulse is transmitted and its echo is mixed with either the transmitted pulse or a local oscillator such that either the pulse timing or its width defines the range gated region. With 100% amplitude modulation, response beyond the gated region is zero, eliminating false alarms from distant objects. Pulse Doppler motion sensors have many desirable attributes, but the prior art fails to teach low-cost high-performance embodiments for the higher microwave frequencies. Clearly, there is a need for a practical implementation at the higher microwave frequencies where compact directional antennas can be employed, and where more spectrum is available. The pulsed RF oscillator and detector of the present invention resolve these prior limitations.

SUMMARY OF THE INVENTION

The present invention provides a microwave pulsed RF oscillator with fast turn on, fast turn off, and well-controlled RF burst width. The oscillator is capable of implementation with controlled amplitude outputs, suppressed spurious modes and a frequency-stable microstrip layout.

The present invention also provides a sensor with a range-limited Doppler response within a region and no response outside that region. Utilizing this technology, a spread-spectrum microwave motion sensor that can be collocated with other spectrum users without having to set a specific operating frequency is achieved.

The oscillator enables a microwave motion sensor with low power consumption, and direction sensing capability. Further embodiments incorporating a novel quadrature antenna, and electronically controllable range, including stepped or multiple range-cell operation are provided.

Accordingly, the present invention comprises a radio frequency oscillator having a first signal path that supplies a bias-on signal at a first time, and a second signal path that supplies a quench signal at a second time after the first time. The oscillator includes an active element that has a first input coupled to the first signal path to receive the bias-on signal, a second input coupled to the second signal path to receive the quench signal. The active element is responsive to the bias-on signal to oscillate at an oscillator frequency and responsive to the quench signal to cease oscillating. The active element comprises a transistor, such as a bipolar transistor or a field effect transistor having a first terminal which is one of a base and a gate, a second terminal which is one of a collector and a drain, and a third terminal which is one of an emitter and a source. In a preferred embodiment, a resistor is connected between the third terminal (emitter/source) and the first signal path, which limits the amplitude of oscillation. Another resistor is connected between the second terminal (collector/drain) and the second signal path which tends to stabilize oscillation of the active element. A first microstrip element is coupled to the first terminal (base/gate). The microstrip is tuned for oscillation at approximately the oscillator frequency. The second microstrip element is coupled to the second terminal (collector/drain), and arranged adjacent the first microstrip element for reactive coupling with the first microstrip element. The second microstrip is tuned for oscillation at approximately the oscillator frequency as well.

The relative timing of the bias-on signal and the quench signal controls the length of the oscillator bursts. The first signal path and the second signal path include circuitry that generate the bias-on and quench signals with precise timing. In one embodiment the bias-on signal comprises a transition on the first signal path from a first voltage level to a second voltage level, such as a first logic level to a second logic level provided by a logic gate. The quench signal in this embodiment comprises a transition on the second signal path from a first voltage level to a second voltage level such as provided by a logic gate.

In one embodiment, the bias-on signal is generated by a first switch, such as a logic gate and the second signal path comprises a delay element and a second switch (in any order) which matches the first switch. A pulse timing signal is supplied to the first switch and through delay element to the second switch, which controls the timing of the RF bursts generated by the oscillator. The width of the burst is determined by the delay element. The delay element located in the path of the quench signal in various embodiments comprises an RC delay element, and an adjustable delay element. Delay can be provided by a variety of circuit implementations, including a sequence of logic gates, a delay line, or other structures known in the art.

Thus, the oscillator in one embodiment includes circuitry for setting an interval between the first time, at which the bias-on signal is asserted and a second time in which the quench signal is asserted. In a preferred embodiment, the interval has a length in a range from about 1 nanosecond to about 100 nanoseconds.

Various embodiments of the oscillator also include a tuning element coupled to one of the first and second microstrip elements in the active device of the oscillator used for tuning the reactive coupling between the first and second microstrip elements. Also, a low value inductor is coupled between the first terminal (base/gate) and a reference node to suppress oscillation at frequencies lower than the oscillator frequency.

Also in various embodiments, the oscillator includes a monopole antenna coupled to one of the first and second microstrips. Further, in another embodiment an antenna reflector, such as a horn antenna having a focal point is included. A structure, such as a printed circuit board, supports the antenna reflector, with the active element and the monopole near the focal point of the reflector.

The present invention also provides a motion sensor which allows for precise range gating and stable oscillator frequency. The motion sensor according to the present invention includes a source of a pulse timing signal, a first signal path including a switch coupled to the source of the pulse timing signal which produces a bias-on signal at a first time, and a second signal path including a delay element, coupled to the source of the pulse timing signal, and a second switch coupled to the delay element which produces a quench signal at a second time after the first time. The active element is implemented as discussed above. The motion sensor also includes a detector which produces an output indicating an echo of the transmit pulse mixing with the transmit pulse itself as it is issued by the oscillator. In various embodiments, the detector comprises a homodyne detector. A homodyne detector can be implemented in one embodiment using a diode having a first terminal at a second terminal. A receive antenna element is coupled to the first terminal of the diode and a capacitive node is coupled to the second terminal of the diode. The voltage on the capacitive node is supplied as output of the motion sensor.

In another embodiment, the motion sensor includes an antenna reflector having a focal point. A transmit antenna element is coupled to the active element of the oscillator and mounted near the focal point of the antenna reflector. A receive antenna element is coupled to the detector and mounted near the focal point of the antenna reflector as well.

In another embodiment, the detector comprises a quadrature detector including an in-phase detector channel and a quadrature detector channel. In an embodiment using an antenna reflector, the transmit antenna element, the first receive antenna element coupled to the in-phase channel, and a second receive antenna element coupled to the quadrature channel are mounted near the focal point of the antenna reflector. The first receive antenna element and the second receive antenna element are trimmed to different lengths to optimize quadrature receive characteristics.

Accordingly the present invention enables a cost-effective, low power, and long lasting electronic sensor that is impervious to harsh environmental conditions such as dirt, rain, snow, acoustic noise, external thermal effects, and sunlight. Furthermore, the sensor of the present invention uses frequencies that can penetrate certain materials (without damaging the material) to allow users to install them behind plastic panels and wood or concrete walls.

Representative uses for the present invention include security alarms, home automation and lighting control, industrial and robotic controls, automatic toilet and faucet control, automatic door openers, vehicle backup warning and collision detection, and general appliance control.

The Doppler passband of the present invention can be set to pass audio and higher frequencies making it responsive to vibrations. As a vibration sensor, the present invention can be used for industrial applications such as wheel and fan blade balancing. It can also be used for shaft vibration sensing, loudspeaker sensing and control, guitar string and musical instrument pickup, and vocal cord vibration sensing.

In another embodiment of the present invention, body organ motion can be detected and monitored, including cardiac motion, arterial pulse, and tongue motion.

Other aspects and advantages of the present invention can be seen on review of the figures, the detailed description and the claims which follow.

BRIEF DESCRIPTION OF THE FIGURES

FIGS. 6A, B, and C show test data for the transmitted RF burst, the range-gated Doppler response, and the range-gated quadrature Doppler response, respectively.

DETAILED DESCRIPTION

Figure 1:
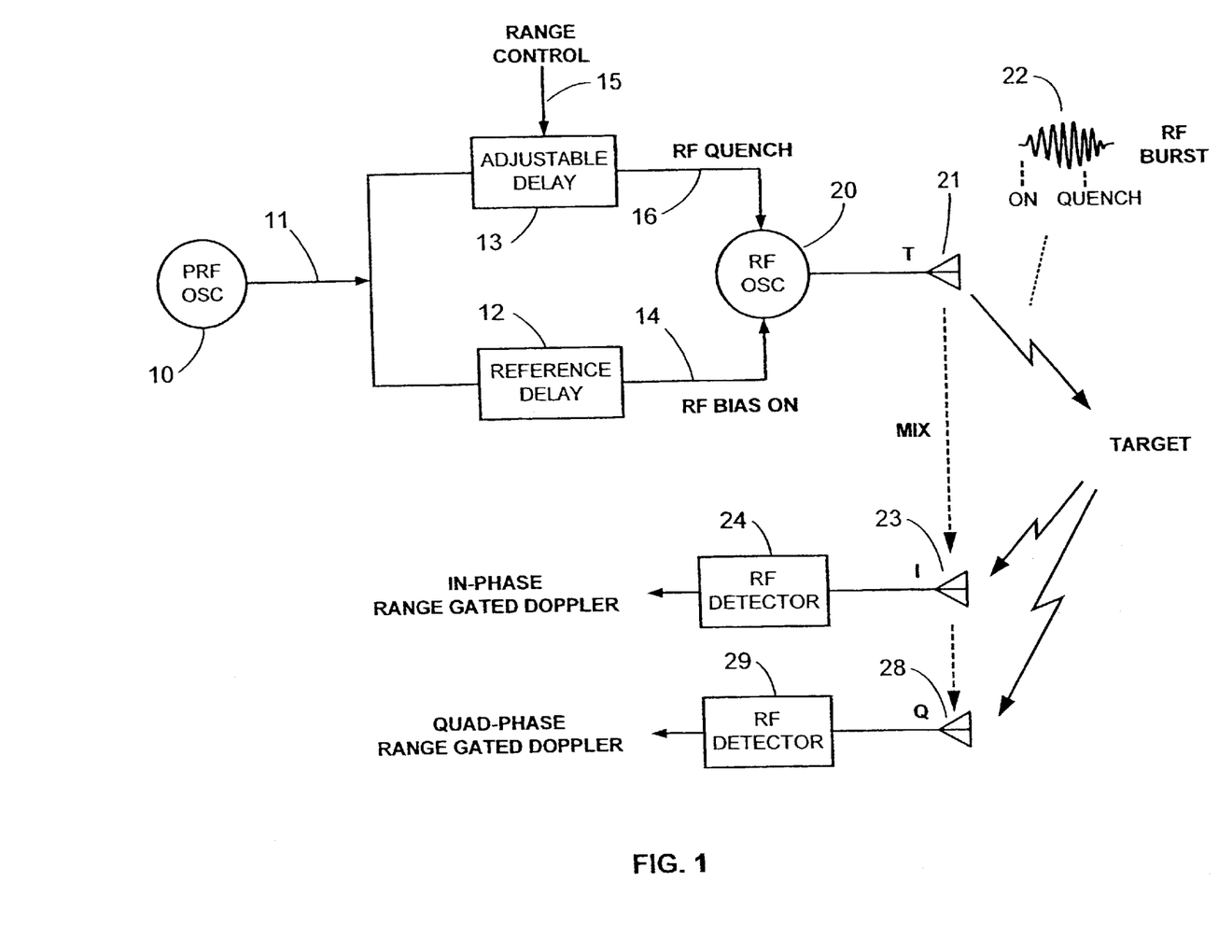
FIG. 1 is a block diagram of a pulsed RF oscillator and radar motion detector according to the present invention.

A detailed description of the present invention is provided below with reference to the figures. FIG. 1 is a block diagram of a pulsed RF oscillator motion sensor according to the present invention. A Pulse Repetition Frequency (PRF) oscillator 10 generates a square wave pulse train on line 11 at 2 MHz in this example providing a pulse timing signal. The frequency of this oscillator 10 may optionally be noise modulated to spread the radiated spectral lines that would otherwise occur with a uniform spacing equal to the PRF. Noise modulation essentially eliminates the possibility of matching PRF interference from other sensors.

The PRF oscillator 10 drives a reference delay path 12 and an adjustable delay path 13. The reference delay path 12 provides a fixed delay, typically on the order of 5-nanoseconds. Its output on line 14 is typically a square-wave which biases on a RF oscillator 20 on the transition from the high to the low level of the squarewave.

The adjustable delay path 13 provides a typical delay adjustment range of 6–105 nanoseconds, depending on the setting 15 of the RANGE CONTROL value. The output 16 of this path is a squarewave whose transition from a high level to a low level biases off or quenches the RF oscillator 20. Thus, the duration of the RF oscillation, i.e., the RF burst, is set by the difference in delays between the upper and lower delay paths. The RF oscillator generates for one example 5.8 GHz RF bursts with a duration of 1–100 ns, depending on the RANGE CONTROL setting.

The RF oscillator 20 is connected to a $\lambda/4$ transmit monopole T 21 preferably located at the focus of a horn antenna or other antenna reflector. In one embodiment, the monopole and horn reside on a low cost printed circuit board (PCB) and produce 8 dB gain at 5.8 GHz.

Antenna T 21 radiates the RF bursts (represented by trace 22) into the sensing region and targets reflect back a portion of the RF energy. A $\lambda/4$ receive monopole I 23 is collocated with the $\lambda/4$ transmit monopole T 21 inside the horn. The horn not only provides gain but also acts as a waveguide beyond cutoff for frequencies below 3 GHz, greatly reducing the chance of interference from cell phones, etc.

The receive monopole I 23 provides a signal to an RF detector 24 that is the sum of the transmitted RF burst and the echo burst from a target. In the preferred embodiment, the RF detector 24 detects the peak RF envelope and substantially holds the peak value from one burst to the next. The directly coupled burst from antenna T 23 is very strong and controls the conduction of the RF detectors. Thus, the detector 24 is only responsive during the burst duration coupled from antenna T 21. Consequently, the RF detector 24 only responds to reflected bursts that return within the duration of the transmitted burst. This action forms a sharp sensing range boundary, or range gate.

The sensor range is defined by the ½ the RF burst width. For echo detection to occur, the echo must return before the transmit pulse ends, otherwise there will be no mixing. The term "mixing" is used loosely here; in reality the echo burst adds or subtracts with a portion of the transmit burst, and the result is peak detected. A multiplying type mixer can be used, but a peak rectifying detector is preferred for simplicity and high output. In either case, sharp oscillator turn-on and turn off is needed to produce a sharp range boundary.

The output of RF detector I is the in-phase range gated Doppler signal produced by a moving target. This signal is amplified by an op amp and provided as a Doppler output for filtering, analog signal processing, or threshold detected for alarm, lighting control or other applications.

A second receive antenna Q 28 and detector channel 29 can be added to provide a range-gated quadrature Doppler output. The I and Q antennas (23, 28) are spaced apart or otherwise phased, such that the I and Q detectors produce Doppler motion signals that are in-phase and quadrature. It should be noted that signals that are in-phase and quadrature at microwave frequencies are also in-phase and quadrature after detection. It is well known in the art that the phase relation between the I and Q Doppler signals can be used to determine target direction. Typically, the I and Q analog signals are threshold detected and applied to the clock and D-input of a flip-flop. The output state of the flipflop then indicates target direction.

Figure 2:
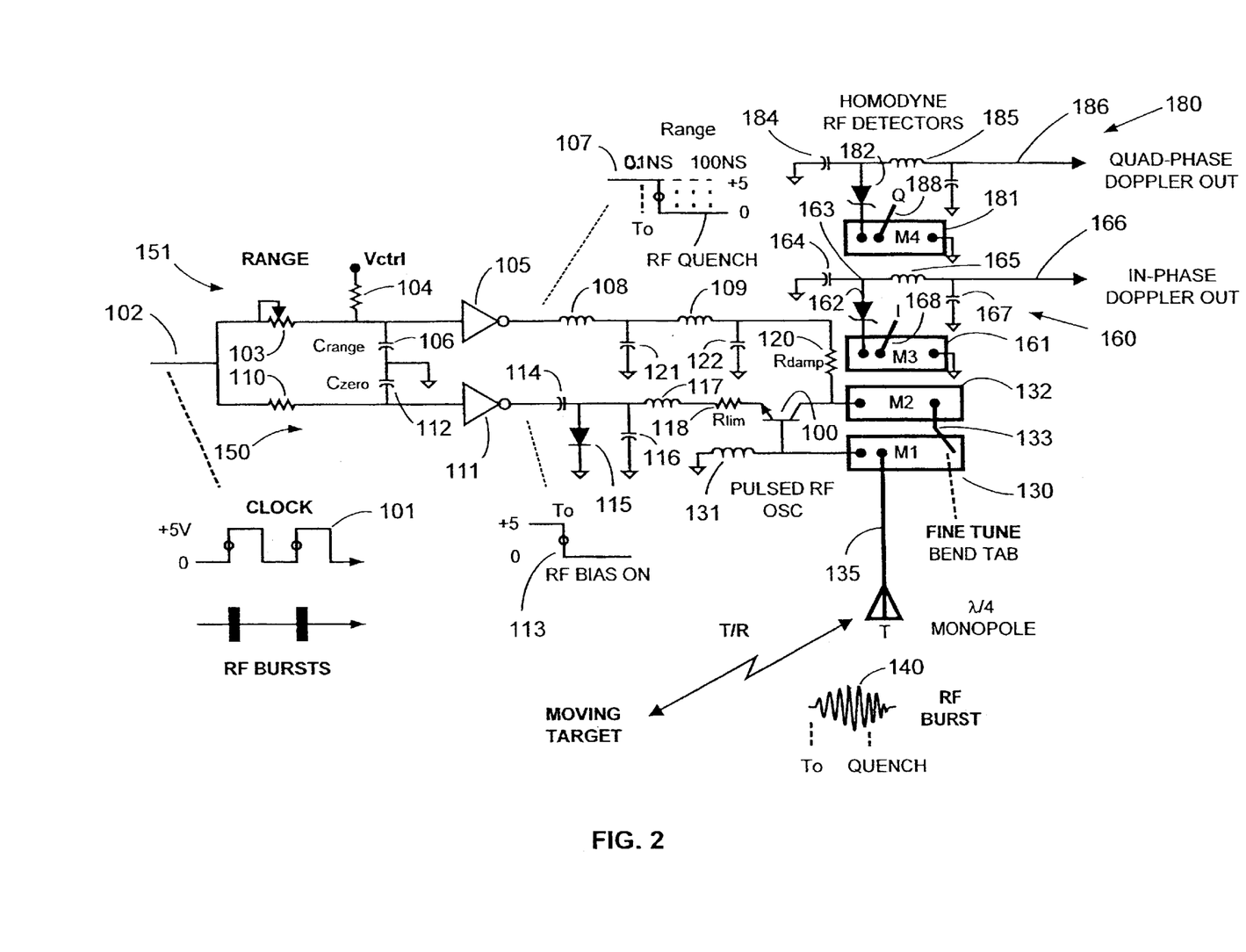
FIG. 2 is a detailed schematic of the present invention employing a bipolar transistor oscillator.

FIG. 2 shows a detailed schematic of the preferred embodiment using a silicon bipolar transistor 100 as the basis of the active element in the RF oscillator. A square-wave pulse repetition frequency PRF clock 101 is supplied on line 102, which drives an upper adjustable delay path and a lower fixed delay path. Typically the PRF is 2 MHz, but may range from about 10 KHz to 100 MHz.

The clock on line 102 is supplied to a first signal path generally 150, and a second signal path generally 151. The first signal path 150 includes resistor 110 which is connected to the input of a inverter 111. A capacitor 112 is connected between the input of the inverter 111 and ground. The output of the inverter 111 provides the bias-on signal 113 on a transition from high to low. The signal is supplied to a first terminal of capacitor 114. The second terminal of the capacitor 114 is coupled to the anode of diode 115. The cathode of diode 115 is connected to ground. Also a capacitor 116 is connected in parallel with the diode 115. An inductor 117 is connected from the second terminal of the capacitor 114 to a limiting resistor 118. The limiting resistor is coupled to the emitter of the bipolar transistor 100.

The second signal path 151 is connected from line 102 to a potentiometer 103. A potentiometer 103 provides the means for adjusting the relative timing of the quench signal generated on the second signal path 151 and the bias-on signal generated on the first signal path 150. Also a control insertion point is provided by resistor 104 which is connected with the potentiometer to the input of inverter 105. A capacitor 106 is connected between the input of inverter 105 and ground. The output of the inverter 105 provides the RF quench signal 107 on a transition from high to low. The RF quench signal 107 is connected through an inductor 108, an inductor 109, and a damping resistor 120 to the collector of the bipolar transistor 100. Capacitors 121 and 122 are connected respectively between the inductors 108 and 109, and between the inductor 109 and the damping resistor 120.

The base of the transistor 100 is connected to a microstrip element 130, and across inductor 131 to ground. The inductor 131 acts as a short for low frequency signals.

The collector of the bipolar transistor 100 is connected to a microstrip element 132 which is arranged for reactive coupling with the microstrip element 130. A fine tuning tab 133 is coupled to the microstrip element 132 and can be bent during manufacture to fine tune reactive coupling between the elements, and stabilize the oscillator frequency. A monopole antenna 135 having a length of about $\lambda/4$ at the oscillator frequency is coupled to the microstrip element 130 in this embodiment. In alternative embodiments, the monopole 135 may be coupled to the microstrip element 132. The monopole is placed at a tap point on the microstrip element 130 which optimizes the loading on the base, and the amplitude of the RF bursts according to the design parameters of a particular implementation.

As shown in FIG. 2, the bias-on signal 113 and the quench signal 107 are basically logic transitions. The relative timing of the logic transitions defines the width of the RF bursts issued by the oscillator. This range is adjustable such that the timing between the transition $T_0$ of the bias-on signal and the transition of the RF quench signal differs by a range of about 1 to 100 nanoseconds. This provides very precise control over the width of the RF bursts represented by trace 140.

In FIG. 2, an in-phase detector generally 160, and a quadrature phase detector generally 180 are illustrated. The in-phase detector 160 includes a microstrip element 161 which is coupled between ground and the cathode of the detector diode 162. The anode of the detector diode 162 is coupled to node 163 which has a capacitive element 164 connected to ground. An inductive element 165 is coupled between the anode of the diode 162 and the output on line 166. The capacitor 167 is coupled between the output 166 and ground. The position of the microstrip element 161 is such that reactive coupling occurs between the transmitted bursts by the oscillator, and the receive bursts. A monopole antenna element 168 is coupled to the microstrip element 161 at a suitable tap point.

The quadrature phase detector is implemented in similar fashion including microstrip element 181, a quadrature monopole 188, a detector diode 182, a capacitor 184, an inductor 185, an output 186, and a capacitor 187.

In the preferred embodiment the delay elements in paths 150 and 151 are RC networks, although other delays means may be used. The range adjustment in the upper path is implemented in this example with a potentiometer 103, and optionally a control voltage injected through a resistor 104 or other digital or analog control. This control voltage affects the delta-V required of the input waveform before reaching the threshold of the logic inverter 105. One use of this injection point 104 is to provide a stepped voltage input to produce time sequenced range settings. Analog switching at the Doppler outputs then steer the Doppler signals into their respective range channels or cells.

The logic invertors 105, 111 are implemented in this example using 1-micron CMOS and provide substantial drive to the RF oscillator. Typically, 74AC04 inverters provide a 12 ohm source impedance with a 0.5 ns transition time.

When the inverter 111 in the lower path 150 goes low, the emitter of the RF oscillator transistor 100 becomes biased ON, and RF oscillations commence immediately. During this time the upper path inverter 105 is at a steady high level, and provides DC bias for the oscillator. A large value coupling capacitor 114 (0.01 uF) and shunt diode 115 in the emitter circuit act as an AC level shift to provide Rlim 118 with a +0.7 to −4.3 V squarewave to bias the emitter on. In this example, resistor 118 Rlim is about 180 ohms and limits and stabilizes the drive level. A well-controlled drive level is desirable to limit unwanted RF harmonic emissions.

The upper path 151 provides a +5 to 0 V transition shortly after the lower path biases the RF oscillator ON. Once the upper path goes to 0 V, the RF oscillator very quickly ceases to oscillate, having lost power. Further, residual ringing and oscillations are quickly damped by collector-base diode conduction in transistor 100 and high junction capacitance at zero bias. In practice, a low-cost silicon bipolar transistor (100) in a SOT-23 package turns ON and OFF with approximately Ins RF envelope transition times at 5.8 GHz.

The use of a two-path gate generator provides for matched inverter delays and can produce very small RF burst widths since the difference between two separate timing edges is relied on and not the minimum pulse width that can be propagated though a single inverter, as would be the case with a single drive line to the RF oscillator.

The RF oscillator in this embodiment is a tuned-base, tuned-collector type oscillator using $\lambda/4$ microstrip elements 132, 130. The microstrips 132, 130 are coupled at their ends with a small capacitance 133 that enhances oscillation and provides a means for fine tuning. A feature of this oscillator is the incorporation of resistors 118, 120 on the order of 50–200Ω into the collector and emitter legs. After extensive experimentation, it was found difficult to produce a fast start oscillator that did not exhibit frequency chirp and pronounced waveform modulation right after start-up. The addition of the resistors 118, 120 eliminated these aberrations. A transmit $\lambda/4$ monopole antenna 135 is tapped onto one of the microstrips 132, 130. Either microstrip 132, 130 can be used to drive the antenna 135, but the base microstrip 130 is preferred. A small value inductor 131 is connected from the base of the transistor 100 to ground to provide a DC return and to reduce the oscillator loop gain at low frequencies. Without a low value inductor 131 (~2 nH), the oscillator may break into a parasitic low frequency oscillation governed by lead parasitics and decoupling elements in conjunction with the microstrips.

In near proximity (~$\lambda/8$), receive $\lambda/4$ I and Q monopoles 168, 188 are situated and coupled to $\lambda/4$ (or shorter) microstrip resonators 161, 181. These resonators 161, 181 drive Schottky detector diodes 162, 182. Typically about 1 V of RF is present during the transmit bursts, and these bursts are peakdetected by the RF detectors. Capacitors 164, 184 connected from the detector diodes to ground set the peak hold characteristics. Not shown are bias resistors to ground, considered part of the Doppler signal processing circuitry, which is well known in the art and not described here. In an alternative embodiment, a conventional RF mixer could be used.

The outputs of the RF detectors are at a DC level that varies in amplitude with the Doppler signal representative of the Doppler frequency difference between the transmit and reflected bursts. The DC level is typically removed with a coupling capacitor, and the final Doppler output is amplified by a baseband amplifier to a convenient level.

Figure 3:
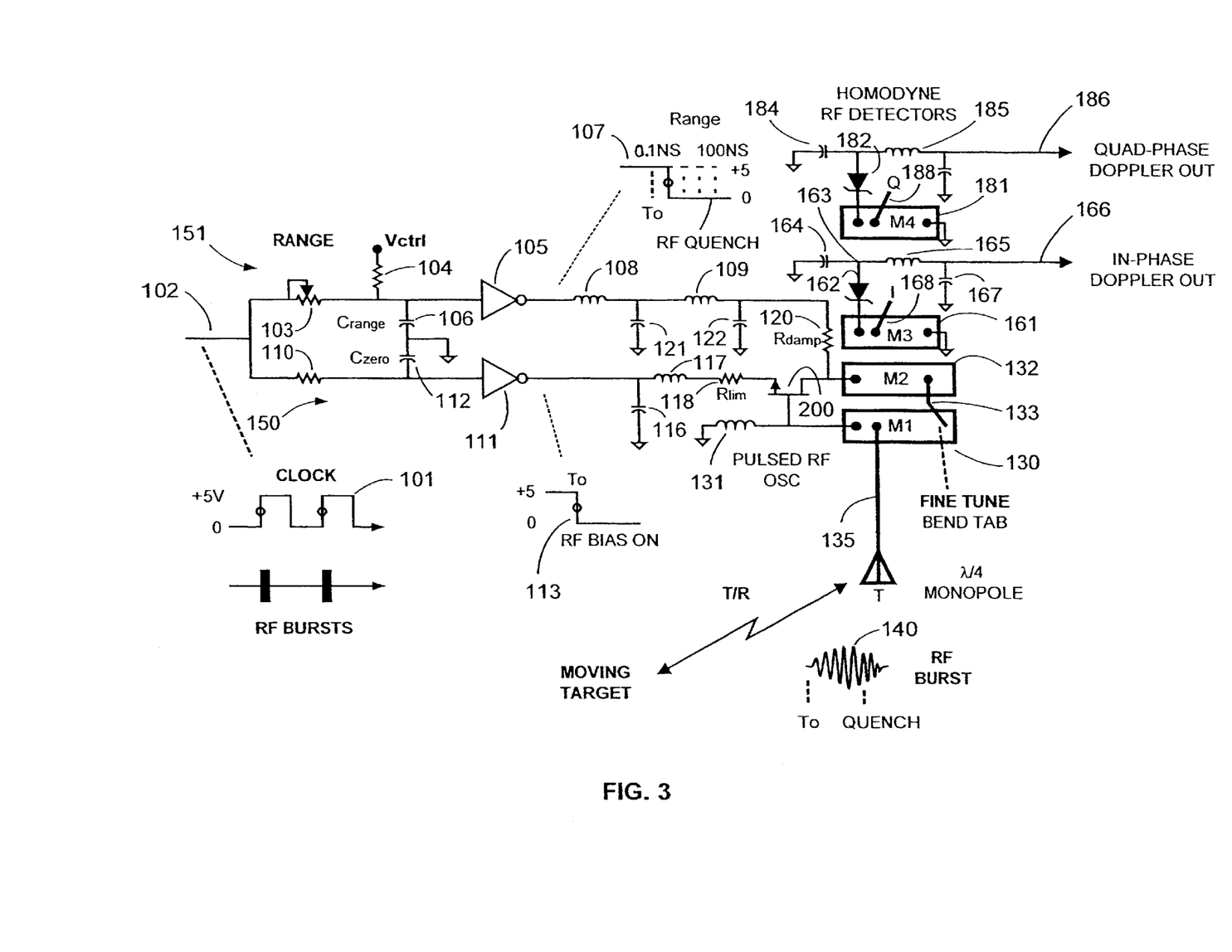
FIG. 3 is a detailed schematic of the present invention employing a FET oscillator.

FIG. 3 shows a detailed schematic of the preferred embodiment using a GaAsFET 200 as the RF oscillator. It is otherwise identical to FIG. 2 (and given like reference numbers) except the AC level shift in the emitter circuit of FIG. 2 (elements 114, 115) has been deleted to suit the +3 to 0-volt bias requirement of the depletion mode GaAsFET.

Figure 4:
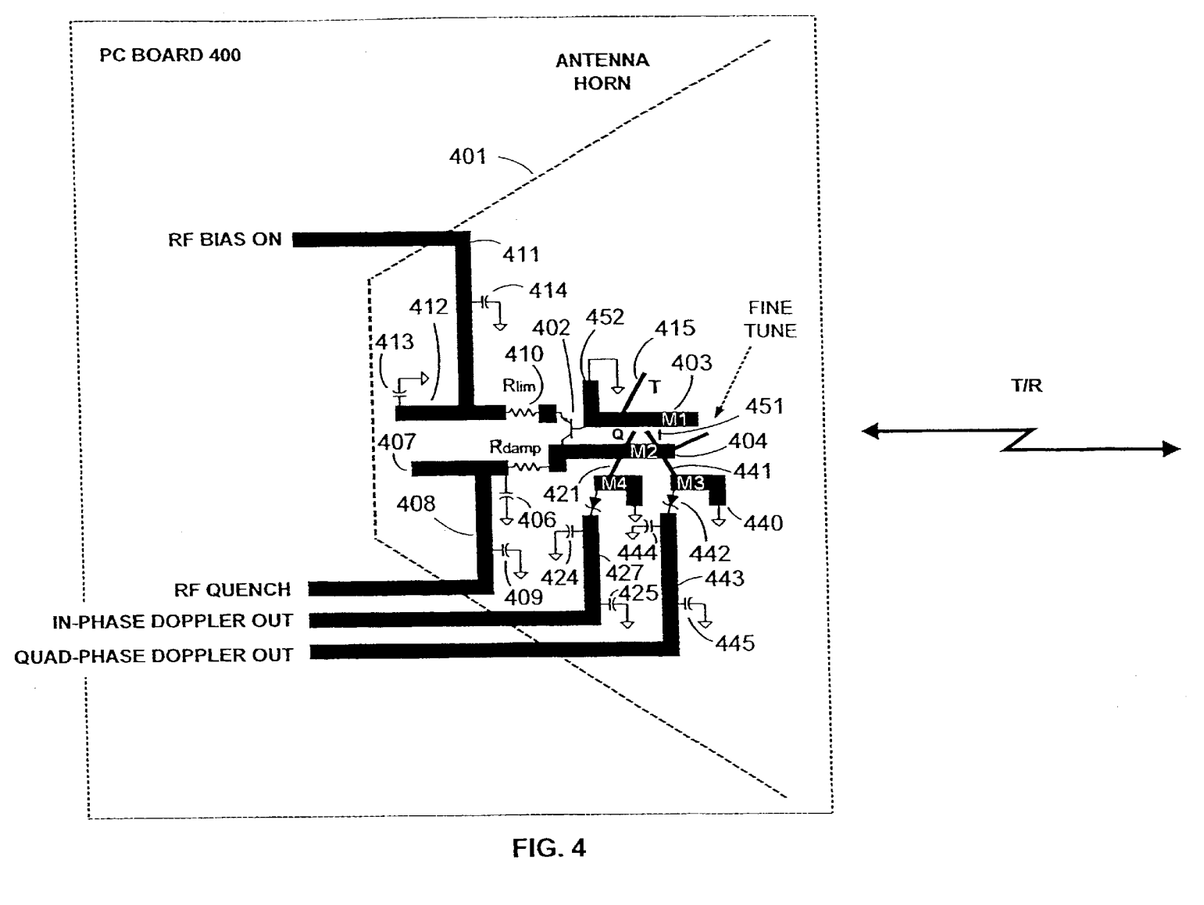
FIG. 4 provides an exemplary RF layout of a quadrature 5.8 GHz radar motion detector.

FIG. 4 provides a plan view of a 5.8 GHz microstrip layout. In FIG. 4, a printed circuit board 400 on which the oscillator is mounted is shown. An antenna horn reflector 401 is mounted on the printed circuit board. The antenna horn reflector 401 has a focal point. Near the focal point of the reflector, the bipolar transistor 402 of the oscillator is mounted. Microstrip M1 403 and microstrip M2 404 are connected to the base and collector respectively of the transistor 402. A damping resistor 405 is connected between the microstrip 404 and trace 408, which is connected at a point near the resistor 405, across capacitor 406 to ground. A microstrip stub 407 on trace 408 provides a bypass RF short, and has a length of about $\lambda/4$. Trace 408 receives the RF quench signal. A capacitor 409 is connected on the trace 408 to ground.

The emitter of the transistor 402 is connected across the limiting resistor 410 to the microstrip trace 411. A microstrip stub 412 having a length of about $\lambda/4$ is connected on one end to trace 411 and on the other end across capacitor 413 and ground. This provides a bypass RF short. A capacitor 414 is connected between the trace 411 and ground. Trace 411 receives the RF bias-on signal.

A transmit monopole 415 is coupled to the microstrip element 403. Inphase and quadrature phase detector channels are also shown in this embodiment. Microstrip elements 420 and 440, for the in-phase and quadrature detectors respectively are mounted close to the microstrip element 404 and grounded on the ends. A monopole element 421 and a monopole element 441 are mounted on suitable tap points on the strips 420 and 440 respectively. The monopole elements 421, 441, and 415 on the transmitter are bent in a pyramid-like shape so that their tips are in close proximity to improve coupling. Detector diodes 422 and 442 are coupled between the microstrip elements 420 and 440 respectively and signal traces 423 and 443. Capacitors 424 and 444 are coupled between the traces 423 and 443 near the diodes 422 and 444 to ground. Similarly, capacitors 425 and 445 are connected to the traces 423 and 444.

The lengths of the microstrip elements 404 and 403 are about $\lambda/4$ to promote oscillation at the oscillator frequency. A tuning tab 451 is coupled to the microstrip element 403 to provide for tuning of the coupling between the microstrips.

Likewise the microstrip elements 420 and 440 are near $\lambda/4$ at the oscillator frequency and length. In this embodiment they are actually shorter than $\lambda/4$ to account for capacitance of the detector diodes 422 and 442.

Thus, the printed circuit board 400 supports the antenna horn 401, and the antenna elements for the transmit and receive path at a location near the focal point of the antenna horn.

Microstrips M1 and M2 (403, 404) are base and collector $\lambda/4$ resonators for the RF oscillator. Their parallel arrangement provides coupling necessary for oscillation. A fine tune wire 451 or metallic tab connected at the end of M2 404 and bent over M1 403 further enhances coupling. Bending this wire allows simple tuning of the oscillator over +/−10% of its center frequency. The base of the transistor 402 has a short microstrip stub 452 connected directly to ground. This serves as a low value inductive short to ground, which eliminates potential sub-harmonic modes that microstrip oscillators are prone to fall into.

The transmit antenna T 415 is coupled to M1 403 at a location that provides a good match. This location is also at or near the focus of the antenna horn 401. In some implementations, the delay path logic circuit and PRF generator are located inside the horn, for compactness.

Microstrips M3 and M4 (420, 440) in conjunction with the capacitance of their RF detector diodes resonate at the 5.8 GHz operating frequency. Antennas I and Q (421, 441) are attached to M3 and M4 to provide signals from antenna T and from the reflected bursts. Antennas Q, T and I are all ~λ/4 monopoles that are bent to a common center at the focus of the horn. Since the monopoles are most responsive at their tips, their phase center is primarily defined by the location of their tips. Thus, their associated circuitry does not need to be precisely collocated to achieve phase quadrature between Q and I. The I and Q antenna lengths are cut slightly below and above λ/4, respectively, to provide a phase quadrature relation at the I and Q Doppler outputs.

The other capacitor and microstrip sections in FIG. 4 generally form low pass filter sections to prevent RF from coupling to the rear of the horn.

Figure 5:
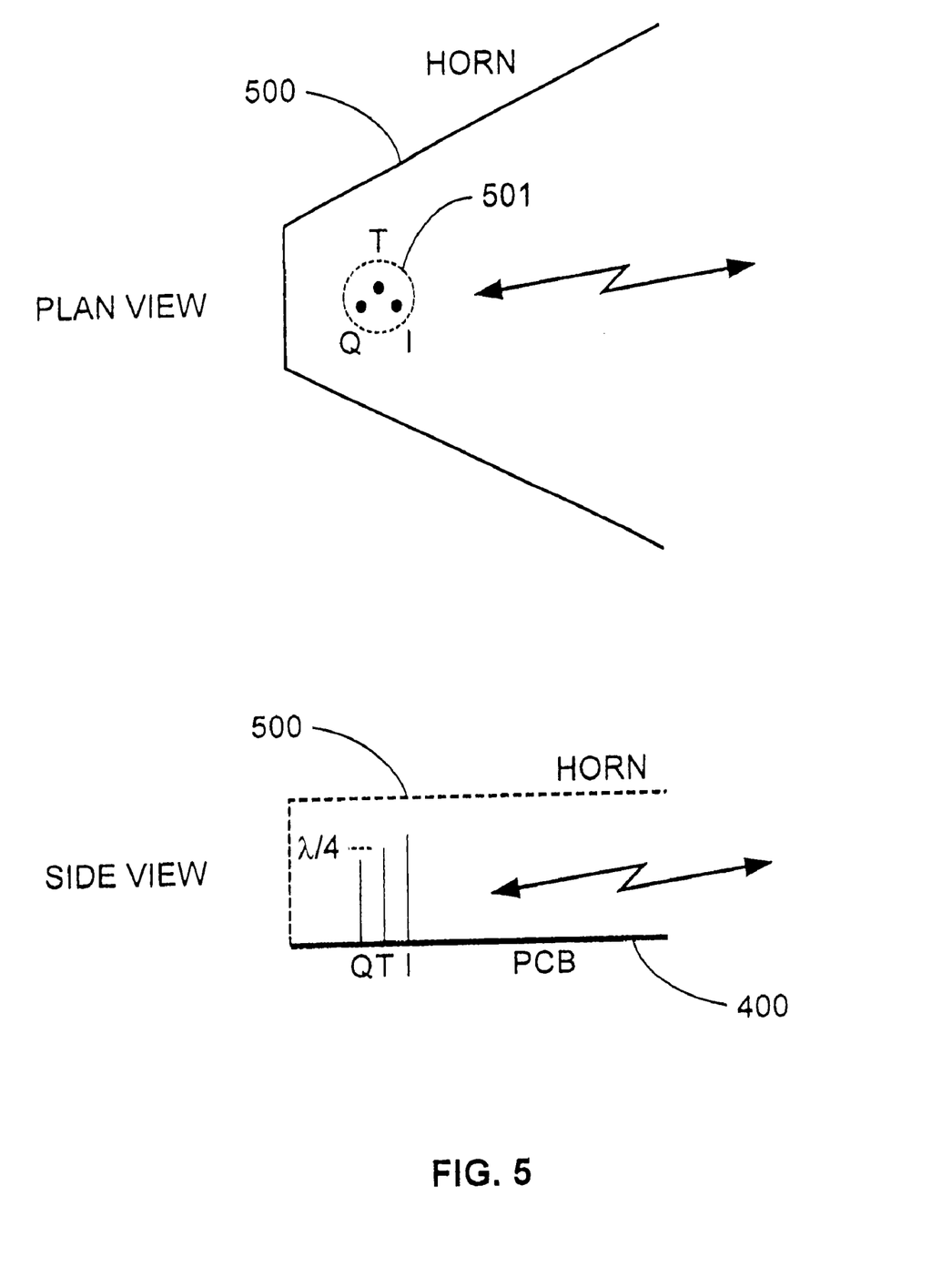
FIG. 5 shows an antenna arrangement for a quadrature motion detector.

FIG. 5 shows the monopole and horn geometry of a preferred embodiment of the present invention. The transmit monopole T and the I and Q receive monopoles are all collocated within less than λ/8 and are at the focus 501 of the horn 500. To achieve a quadrature relation between the I and Q monopoles, one is cut slightly below resonance and the other slightly above resonance, as can be seen in the side view, providing a 90° phase relationship. Experiments show that this tight physical arrangement provides identical direction sensing capability as I and Q antennas physically separated by λ/4. However, if they were separated by λ/4, both of them could not be at the focus of the horn, and they would exhibit different gain and beam patterns. This invention solves that problem.

Figure 6A:
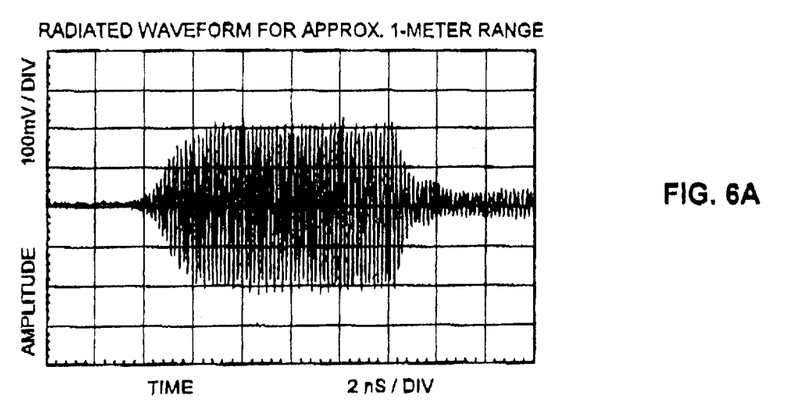

The radiated RF burst data in FIG. 6A shows a sharp envelope risetime and falltime produced by the RF oscillator. Both transition times are on the order of a nanosecond. The pulse width is ~8 ns, corresponding to a sensing distance of 4-feet. Without the oscillator damping resistor, the flat portion of the burst becomes modulated depending on tuning conditions and temperature.

Figure 6B:
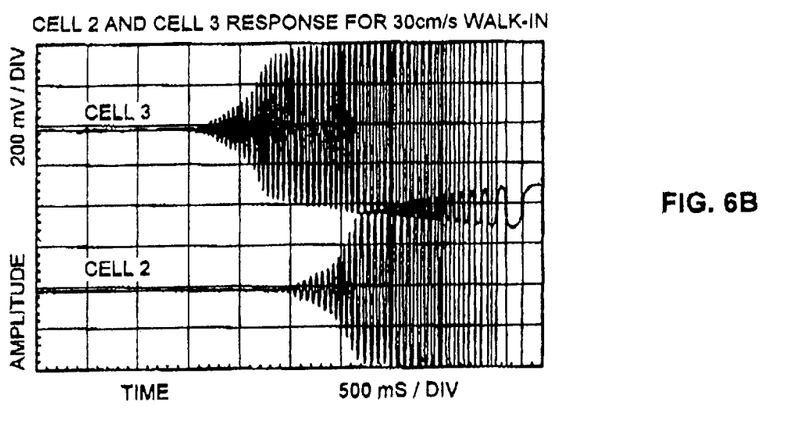

FIG. 6B shows the in-phase Doppler output for two different settings of the RANGE CONTROL. In this case, an electronically switched voltage alternating between two different levels provided the range control. The inphase Doppler output was then amplified and routed through a demultiplexer to range channels, or cells. Each cycle in the plot corresponds to motion through λ/2 or about 2.5 cm for a 5.8 GHz sensor. The portions of the plot with no response lie outside the range-gated region. A 0.5 m square plate was used as a target and was moved inbound at a 30 cm/sec rate. Zero range is at the right of the plot.

Figure 6C:
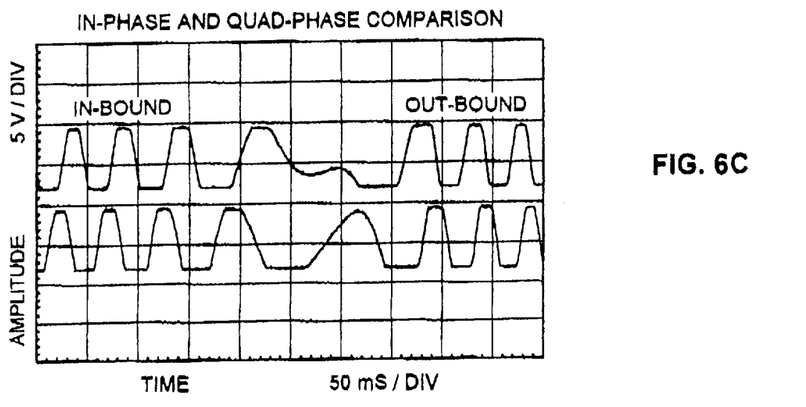

In-phase and quadrature signatures can be seen in FIG. 6C. Moving a metal plate in-bound and then out-bound produced them. The viewer should carefully compare the phase relation between the in-bound and out-bound regions, noting the level of the lower trace during the positive transitions of the upper trace. Typically the upper trace is applied to the clock input of a flip-flop which toggles on the positive transitions. The lower trace is applied to the D-input of the flip-flop, and its level is clocked to the Q output to indicate target direction.

In summary, a pulsed RF Oscillator and sensor are based on: 1) A BIAS-ON path for controllably turning on an RF oscillator, 2) a QUENCH path having a delayed timing relation to the BIAS-ON path for controllably turning off an RF oscillator, and 3) an RF oscillator responsive to the BIAS-ON and QUENCH paths that produces an RF burst with a width related to the timing between the BIAS-ON and QUENCH paths.

Various features of the oscillator include:

BIAS-ON and QUENCH signals are stepped voltages.

BIAS-ON and QUENCH signals are directly derived from logic elements.

Delay path incorporates an RC delay element.

The BIAS-ON and QUENCH paths utilize matched delay logic or transistor elements.

The RF oscillator amplitude is set by a current limiting resistor.

The RF oscillator is stabilized with a resistor in the collector or drain circuit.

The RF oscillator employs microstrip resonators in the collector/drain and base/gate circuits.

The RF oscillator employs a low value inductance in the base/gate circuit to eliminate spurious low frequency modes.

The RF oscillator directly drives a monopole antenna element from the base/gate or collector/drain microstrip.

The RF oscillator and monopole are located at the focus of a reflector or horn antenna.

The RF oscillator produces RF bursts at the PRF.

A pulse Doppler motion sensor according to various implementations of the present invention comprises: 1) a dual path pulsed RF oscillator, and 2) a homodyne RF detector responsive to transmitted RF bursts from the RF oscillator and echo bursts, where the RF burst width defines the range-gated region.

Features of various embodiments of the sensor include:

RF homodyne detector employing a single detector diode.

RF homodyne detector employing a microstrip resonator connected to a monopole antenna.

quadrature channel (for direction sensing, etc).

collocated quadrature monopoles at λ/4 spacing.

quadrature I and Q monopoles with substantially less than λ/4 spacing and cut to different lengths for the purpose of controlling the accuracy of phase quadrature.

multiple or variable range cell operation implemented by means of a voltage controlled delay in the quench path.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A radio frequency oscillator, comprising:

a first signal path supplying a bias-on signal at a first time;

a second signal path supplying a quench signal at a second time after the first time; and an active element having a first input coupled to the first signal path, a second input coupled to the second signal path, and responsive to the bias-on signal to oscillate at an oscillator frequency, and responsive to the quench signal to cease oscillating at the oscillator frequency.

2. The oscillator of claim 1, wherein the bias-on signal comprises a transition on the first signal path from a first voltage level to a second voltage level.

3. The oscillator of claim 1, wherein the quench signal comprises a transition on the second signal path from a first voltage level to a second voltage level.

4. The oscillator of claim 1, wherein the first signal path comprises a digital gate which supplies logic level outputs, and wherein the bias-on signal comprises a transition on the first signal path from a first logic level to a second logic level at the first time.

5. The oscillator of claim 1, including circuitry for setting an interval between the first time and the second time.

6. A radio frequency oscillator, comprising:
    a first signal path supplying a bias-on signal at a first time;
    a second signal path supplying a quench signal at a second time after the first time;
    an active element having a first input coupled to the first signal path, a second input coupled to the second signal path, and responsive to the bias-on signal to oscillate at an oscillator frequency, and responsive to the quench signal to cease oscillating at the oscillator frequency; and
    circuitry for setting an interval between the first time and the second time, wherein the interval has a length in a range from about 1 nanosecond to about 100 nanoseconds.

7. A radio frequency oscillator, comprising:
    a first signal path supplying a bias-on signal at a first time;
    a second signal path supplying a quench signal at a second time after the first time;
    an active element having a first input coupled to the first signal path, a second input coupled to the second signal path, and responsive to the bias-on signal to oscillate at an oscillator frequency, and responsive to the quench signal to cease oscillating at the oscillator frequency; and
    a source of a pulse timing signal; and wherein
    the first signal path includes a first switch coupled to the source of the pulse timing signal, which produces the bias-on signal; and
    the second signal path includes a delay element, coupled to the source of the pulse timing signal, and a second switch coupled to the delay element which produces the quench signal.

8. The oscillator of claim 7, wherein the delay element comprises a RC delay element.

9. The oscillator of claim 7, wherein the delay element comprises an adjustable delay element.

10. The oscillator of claim 7, wherein the first and second switches comprise transistors which match so that variations in performance are reduced.

11. A radio frequency oscillator, comprising:
    a first signal path supplying a bias-on signal at a first time;
    a second signal path supplying a quench signal at a second time after the first time;
    an active element having a first input coupled to the first signal path, a second input coupled to the second signal path, and responsive to the bias-on signal to oscillate at an oscillator frequency, and responsive to the quench signal to cease oscillating at the oscillator frequency; and wherein the active element comprises a transistor having a first terminal which is one of a base and a gate, the second terminal which is one of a collector and a drain, and a third terminal which is one of an emitter and source.

12. The oscillator of claim 11, including:
    a resistor connected between the third terminal and the first signal path, which limits amplitude of the oscillation.

13. The oscillator of claim 11, including:
    a resistor connected between the second terminal and the second signal path which tends to stabilize the oscillation.

14. The oscillator of claim 11, including:
    a microstrip element coupled to the second terminal, the microstrip tuned for approximately one-quarter wavelength at the oscillator frequency.

15. The oscillator of claim 11, including:
    a microstrip element coupled to the first terminal, the microstrip tuned for approximately one-quarter wavelength at the oscillator frequency.

16. The oscillator of claim 11, including:
    a first microstrip element coupled to the first terminal, the first microstrip tuned for oscillation at approximately the oscillator frequency; and
    a second microstrip element coupled to the second terminal arranged adjacent to the first microstrip element for reactive coupling with the first microstrip element.

17. The oscillator of claim 16, including a tuning element coupled to one of the first and second microstrip elements for tuning the reactive coupling between the first and second microstrip elements.

18. The oscillator of claim 11, including:
    an inductor coupled between the first terminal and a reference node to suppress oscillation at frequencies lower then be oscillator frequency.

19. A radio frequency oscillator, comprising:
    a first signal path supplying a bias-on signal at a first time;
    a second signal path supplying a quench signal at a second time after the first time;
    an active element having a first input coupled to the first signal path a second input coupled to the second signal path, and responsive to the bias-on signal to oscillate at an oscillator frequency, and responsive to the quench signal to cease oscillating at the oscillator frequency; and wherein the active element comprises a bipolar transistor.

20. A radio frequency oscillator, comprising:
    a first signal path supplying a bias-on signal at a first time;
    a second signal path supplying a quench signal at a second time after the first time;
    an active element having a first input coupled to the first signal path, a second input coupled to the second signal path, and responsive to the bias-on signal to oscillate at an oscillator frequency, and responsive to the quench signal to cease oscillating at the oscillator frequency; and wherein the active element comprises a field effect transistor.

21. The oscillator of claim 20, wherein the active element comprises a GaAs field effect transistor.

22. A radio frequency oscillator, comprising:
    a first signal path supplying a bias-on signal at a first time;
    a second signal path supplying a quench signal at a second time after the first time;
    an active element having a first input coupled to the first signal path, a second input coupled to the second signal path, and responsive to the bias-on signal to oscillate at an oscillator frequency and responsive to the quench signal to cease oscillating at the oscillator frequency; and including a monopole antenna coupled to the oscillator.

23. The oscillator of claim 11, including:
    a monopole antenna coupled to one of the first and second terminals of the transistor.

24. The oscillator of claim 16, including a monopole antenna coupled to the first microstrip.

25. The oscillator of claim 16, including a monopole antenna coupled to the second microstrip.

26. The oscillator of claim 23, including an antenna reflector having a focal point, and a structure supporting the antenna reflector, and supporting the active element and the monopole antenna at or near the focal point.

27. A radio frequency oscillator, comprising:

a first signal path including a first switch which produces a bias-on signal at a first time; and a second signal path including a delay element and a second switch coupled to the delay element which produces a quench signal at a second time after the first time;

an active element having a first input coupled to the first signal path, a second input coupled to the second signal path, and responsive to the bias-on signal to oscillate at an oscillator frequency, and responsive to the quench signal to cease oscillating at the oscillator frequency, wherein the active element comprises a transistor having a first terminal which is one of a base and a gate, a second terminal which is one of a collector and a drain, and a third terminal which is one of an emitter and a source, and a resistor connected between the third terminal and the first signal path, which limits amplitude of the oscillation;

a resistor connected between the second terminal and the second signal path which tends to stabilize the oscillation;

a first microstrip element coupled to the first terminal, the microstrip tuned for oscillation at approximately the oscillator frequency, a second microstrip element coupled to the second terminal arranged adjacent to the first microstrip element for reactive coupling with the first microstrip element, the second microstrip tuned for oscillation at approximately the oscillator frequency.

28. The oscillator of claim 27, wherein the bias-on signal comprises a transition on the first signal path from a first voltage level to a second voltage level.

29. The oscillator of claim 27, wherein the quench signal comprises a transition on the second signal path from a first voltage level to a second voltage level.

30. The oscillator of claim 27, wherein the switch in the first signal path comprises a digital gate which supplies logic level outputs, and wherein the bias-on signal comprises a transition on the first signal path from a first logic level to a second logic level at the first time.

31. The oscillator of claim 27, including circuitry for setting an interval between the first time and the second time.

32. The oscillator of claim 31, wherein the interval has a length in a range from about 1 nanosecond to about 100 nanoseconds.

33. The oscillator of claim 27, including a source of a pulse timing signal; and a circuit connecting the pulse timing signal to the delay element in the second signal path and to the switch in the first signal path.

34. The oscillator of claim 27, including a tuning element coupled to one of the first and second microstrip elements for tuning the reactive coupling between the first and second microstrip elements.

35. The oscillator of claim 27, including:

an inductor coupled between the first terminal and a reference node to suppress oscillation at frequencies lower than the oscillator frequency.

36. The oscillator of claim 27, wherein the active element comprises a bipolar transistor.

37. The oscillator of claim 27, wherein the active element comprises a field effect transistor.

38. The oscillator of claim 27, wherein the active element comprises a GaAs field effect transistor.

39. The oscillator of claim 27, including a monopole antenna coupled to the first microstrip.

40. The oscillator of claim 27, including a monopole antenna coupled to the second microstrip.

41. The oscillator of claim 27, including a monopole element coupled to one of the first and second microstrips, an antenna reflector having a focal point, and a structure supporting the antenna reflector, and supporting the active element and the monopole element at or near the focal point.

42. A motion sensor, comprising:

a source of a pulse timing signal;

a first signal path including a first switch coupled to the source of the pulse timing signal, which produces a bias-on signal at a first time;

a second signal path including a delay element, coupled to the source of the pulse timing signal, and a second switch coupled to the delay element which produces a quench signal at a second time after the first time;

an active element having a first input coupled to the first signal path, a second input coupled to the second signal path, and responsive to the bias-on signal to oscillate at an oscillator frequency, and responsive to the quench signal to cease oscillating at the oscillator frequency to produce a transmit pulse having a pulse width determined by the first and second times and a pulse repetition pattern determined by the pulse timing signal; and a detector which produces an output indicating an echo of a transmit pulse mixing with the transmit pulse.

43. The motion sensor of claim 42, wherein the detector comprises a homodyne detector.

44. The motion sensor of claim 42, wherein the detector comprise a diode having a first terminal and a second terminal, a receive antenna element coupled to the first terminal of the diode, and a capacitive node coupled to the second terminal of the diode.

45. The motion sensor of claim 42, including circuitry coupled to the second signal path for setting an interval between the first time and the second time.

46. The motion sensor of claim 45, wherein the interval has a length in a range from about 1 nanosecond to about 100 nanoseconds.

47. The motion sensor of claim 42, wherein the delay element comprises a RC delay element.

48. The motion sensor of claim 42, wherein the delay element comprises an adjustable delay element.

49. The motion sensor of claim 42, including:

an antenna reflector having an focal point;

a transmit antenna element coupled to the active element and mounted near the focal point of the antenna reflector;

a receive antenna element coupled to the detector and mounted near the focal point of the antenna reflector.

50. The motion sensor of claim 42, wherein the detector comprises a quadrature detector, having an in-phase detector channel and a quadrature detector channel.

51. The motion sensor of claim 42, wherein the detector comprises a quadrature detector, having an in-phase channel and a quadrature channel, and including:

an antenna reflector having an focal point;

a transmit antenna element coupled to the active element and mounted near the focal point of the antenna reflector;

a first receive antenna element coupled to the in-phase channel of the detector and mounted near the focal point of the antenna reflector; and a second receive antenna element coupled to the quadrature channel of the detector and mounted near the focal point of the antenna reflector.

52. The motion sensor of claim 51, wherein the first and second receive antenna elements comprise respective monopoles.

53. The motion sensor of claim 52, wherein the monopoles of the first and second receive antennas have different lengths.

54. The motion sensor of claim 42, wherein the detector comprises a quadrature detector, having an in-phase channel and a quadrature channel, and including:

a transmit antenna element coupled to the active element;

a first receive antenna element coupled to the in-phase channel of the detector; and a second receive antenna element coupled to the quadrature channel of the detector.

55. The motion sensor of claim 54, wherein the first and second receive antenna elements comprise respective monopoles.

56. The motion sensor of claim 55, wherein the monopoles of the first and second receive antennas are spaced about one-quarter wavelength at the transmit frequency from one another.

57. A radio frequency oscillator, comprising:

a first signal path supplying a bias-on signal at a first time;

a second signal path supplying a quench signal at a second time after the first time;

an active element having a first input coupled to the first signal path, a second input coupled to the second signal path, and responsive to the bias-on signal to oscillate at an oscillator frequency, and responsive to the quench signal to cease oscillating at the oscillator frequency; and wherein the first signal path includes a first switch which produces the bias-on signal; and the second signal path includes a delay element and a second switch coupled to the delay element which produces the quench signal, and wherein the first switch matches the second switch.

* * * * *